United States Patent
Soane et al.

(10) Patent No.: US 6,821,458 B2
(45) Date of Patent: Nov. 23, 2004

(54) NEAR-NET-SHAPE POLYMERIZATION PROCESS AND MATERIALS SUITABLE FOR USE THEREWITH

(75) Inventors: David S. Soane, Piedmont, CA (US); Michael R. Houston, Eagle River, WI (US); Toshiaki Hino, Berkeley, CA (US)

(73) Assignee: ZMS, LLC, Emeryville, CA (US)

( * ) Notice: Subject to any disclaimer, the term of this patent is extended or adjusted under 35 U.S.C. 154(b) by 19 days.

(21) Appl. No.: 10/004,453

(22) Filed: Dec. 5, 2001

(65) Prior Publication Data

US 2002/0120067 A1 Aug. 29, 2002

Related U.S. Application Data

(63) Continuation-in-part of application No. 09/511,661, filed on Feb. 22, 2000, now Pat. No. 6,380,314, which is a continuation-in-part of application No. PCT/US99/22048, filed on Sep. 22, 1999
(60) Provisional application No. 60/101,285, filed on Sep. 22, 1998.

(51) Int. Cl.[7] .............................................. B29D 11/00
(52) U.S. Cl. .......................... 264/1.1; 359/642; 525/242
(58) Field of Search .......................... 264/1.1; 359/642; 525/242, 244, 292

(56) References Cited

U.S. PATENT DOCUMENTS

| | | | |
|---|---|---|---|
| 3,557,046 A | * | 1/1971 | Muskat .......................... 524/533 |
| 4,131,625 A | | 12/1978 | Arnold et al. |
| 4,402,887 A | | 9/1983 | Kuriyama et al. |
| 4,510,593 A | | 4/1985 | Daniels |
| 4,524,162 A | | 6/1985 | Domeier |
| 4,785,064 A | | 11/1988 | Hegel |
| 5,110,514 A | | 5/1992 | Soane |
| 5,114,632 A | | 5/1992 | Soane |
| 5,185,234 A | * | 2/1993 | Nakatsukasa et al. .... 430/284.1 |
| 5,278,243 A | | 1/1994 | Soane |
| 6,140,450 A | * | 10/2000 | Ishikawa et al. .............. 528/25 |

FOREIGN PATENT DOCUMENTS

| | | |
|---|---|---|
| EP | 0106641 | 4/1984 |
| EP | 0238863 | 9/1987 |
| GB | 498679 | 1/1939 |
| GB | 577432 | 5/1946 |
| GB | 2257978 A | 1/1993 |

OTHER PUBLICATIONS

PCT International Search Report for appln. PCT/US99/22048.

* cited by examiner

Primary Examiner—Jeffrey Mullis
(74) Attorney, Agent, or Firm—M. Henry Heines; Townsend and Townsend and Crew LLP; Jacqueline S. Larson

(57) ABSTRACT

This disclosure describes a processing approach for the rapid and efficient in-situ polymerization of specially prepared precursor mixtures to achieve near-net-shape production of objects/articles with exact dimensions. The process relies on the use of polymerizable compositions comprised of a mixture of a dead polymer, a reactive plasticizer and an initiator, which compositions are semi-solid-like prior to curing and induce low shrinkage upon curing as a result of their partially polymerized nature prior to processing. The partially polymerized nature of the precursor mixtures also allows extremely impact-resistant objects/articles to be fabricated. Other desirable engineering property attributes can similarly be achieved via the judicious blending of starting ingredients in formulating the polymerizable (curable) mixtures.

11 Claims, No Drawings

NEAR-NET-SHAPE POLYMERIZATION PROCESS AND MATERIALS SUITABLE FOR USE THEREWITH

CROSS REFERENCE TO RELATED APPLICATIONS

This application is a continuation-in-part application of U.S. application Ser. No. 09/511,661, filed on Feb. 22, 2000 now U.S. Pat. No. 6,380,314, which is a continuation-in-part application of International patent application No. PCT/US99/22048, filed on Sep. 22, 1999 and designating the United States, which claims the benefit of U.S. Provisional Patent Application Ser. No. 60/101,285, filed on Sep. 22, 1998; the disclosures of all of which are incorporated herein by reference in their entirety.

FIELD OF THE INVENTION

This invention is related to the fields of polymerization and molding. More particularly, it is related to a process for the rapid in-situ near-net-shape polymerization of semi-solid-like materials to provide objects that are dimensionally stable and precise, with very little shrinkage upon curing. The invention is further related to semi-solid-like materials useful with the process.

BACKGROUND OF THE INVENTION

Dimensionally precise objects/articles find numerous applications in electronics, optics, automotive, aerospace, and other high-technology industries. Examples include optically transparent objects/articles such as various precision lenses (spherical and aspherical), ophthalmic lenses (single vision, bifocal, trifocal, and progressive), contact lenses, optical data storage disk substrates, and projection optics/lens arrays. Non-transparent but dimensionally exact parts abound, such as couplers, housings, gears, and various packaging assemblies. The most straightforward fabrication method for dimensionally precise parts is the machining, grinding, and polishing of sheet stock and, in fact, this approach is still used today for some types of ophthalmic lenses. Unfortunately, this approach is limited to simple geometries and is costly due to the relatively large amounts of skilled labor required to produce a single part. More commonly, the plastics industry relies on well-known processes such as injection molding, compression molding, transfer molding, reactive injection molding (RIM), and casting for the fabrication of geometrically complex parts.

Injection molding, compression molding and transfer molding require the use of thermoplastic polymers. Material choices are limited to uncrosslinked polymers that can be melted by heat and injected at high pressures. Example polymers include polymethylmethacrylate, polystyrene, ABS (acrylonitrile-butadiene-styrene) and polycarbonate. These molding processes entail high temperature and pressure; therefore, expensive molding equipment and molds are necessary. Large parts with thick cross-sections are difficult to mold, since the heat transfer rate is slow. Long cycle times make the processes uneconomical. Additionally, finite coefficients of thermal expansion can lead to part warpage upon cooling. Thus, these processes are seldom practical for large-scale manufacturing of truly dimensionally demanding parts.

Reaction injection molding requires the use of at least two highly reactive components (A+B). Urethane is one such example, where the reactive components are monomeric isocyanates and alcohols. The components are quickly and thoroughly mixed just before injection into the mold cavity. The material is then allowed to quickly set in the cavity (cured). This methodology relies on materials that are highly reactive and generally toxic. Mechanical means for thorough mixing is part of the integral process, making the production equipment costly. The fabricated parts are also not quite dimensionally exact due to shrinkage effects associated with the polymerization process. Material selection is limited by the required reaction chemistry, as well. Thus, reactive injection molding (RIM) is limited by the need for highly reactive functional groups, the intensity of mixing prior to mold fill, and complex and expensive machinery to carry out the process.

Fabrication of precision parts has been attempted by processes generally known as casting. Casting is typically a less expensive alternative to the above processes. It is also a more flexible process, in that a great number of precursor mixtures (e.g., monomers, crosslinkers, oligomers, etc.) can be formulated to achieve different final parts and performance properties. The final parts can be thermosets, formed by a polymer network that is crosslinked to prevent melt flow. Since the precursor solution has a relatively low viscosity to facilitate mold fill, the process is a low-pressure operation, reducing the necessary equipment cost. The casting process, unfortunately, is often compromised by the high shrinkage rate of the formulated precursor mixtures, yielding inexact parts with warped shapes. The high shrinkage rate is a natural consequence of using precursors that have low to moderate viscosities. If we take an ophthalmic lens as an example, the mold defining the lens-shaped cavity generally consists of a front and a back half, and an intervening gasket. The front mold half is concave, whereas the back mold half is convex. Detailed design features distinguish the utility of the resulting lens. Hence, simple vision, bifocal, trifocal, progressive, spherical, aspherical, and toroidal lenses can all be made, in principle, but if and only if the in-situ curing process can be performed with near net-shape fidelity. This is obviously a difficult task, at best, if the material used for casting exhibits a high degree of shrinkage. Casting thus requires a mold-filling step, an activation step to trigger and sustain polymerization, and a mold-opening/ensuing cleaning step to finish the part and to recycle/re-shelf the mold halves. To date, all known casting processes begin with a polymerizable fluid that can be easily fed into the mold cavity, i.e., at moderate pressures. Care is necessary to minimize bubble creation. A carefully designed gasket is required, applied to seal off the cavity formed by the mold halves. Then a controlled curing step is imposed to convert the liquid feed into a finished, solid object.

Most curable formulations contain carbon-carbon double bonds. Such unsaturated sites are exemplified by functional groups like acrylates, methacrylates, vinyl ethers, and vinyls. Free radical or ionic polymerization mechanisms can be induced by the appropriate initiators, triggered by either UV or heat, i.e., photo- or thermally-induced polymerization. Since the reaction mixtures must fill the cavities in as short a time as possible to allow reasonable process economies, small-molecule or oligomeric mixtures are usually employed to keep viscosities low. These systems have a significant degree of shrinkage upon cure, as high as 15% for some oligomeric mixtures, and even greater than 20% for some small molecule formulations.

Additionally, the polymerization of unsaturated species is unfortunately an exothermic reaction. When such a reactive system is cured a great deal of heat is generated. The result is a spurious temperature excursion of the cast part during cure which often leads to thermal degradation of the material, discoloration, and part warpage upon cool down and removal from the mold. This problem may be reduced by improving heat transfer. Unfortunately, heat transfer can be improved only so much, due in part to the poor thermal conductivity of most polymeric systems. Overheating during cure can also be reduced by lowering the concentration of initiator species in the starting formulation, except that decreasing the initiator concentration prolongs the curing process and can lead to incomplete curing reactions and only partially polymerized final objects.

The heat generation and shrinkage accompanying polymerization must be accommodated by specially engineered curing processes, such as zone-curing techniques, in order to produce exact parts that replicate the contours of the cavity, and to slow the curing reaction so as to reduce spurious temperature rises. The need to use a gasket to prevent leakage (material escape) and minimize introduction of air bubbles dictates limited flexibility of mechanical design. It is also difficult to have the front and back mold halves positioned in such a way so as to intentionally create a non-aligned axial offset (known as de-centration). In addition, it is difficult to have the two axes rotated to create an intentional tilt (thus introducing a prismatic effect to the ensuing lens).

Finally, since most if not all of the reactive mixture exists initially in an unpolymerized state, the process must accomplish the curing of all such as-yet unreacted material precursors so that no small-molecule, volatile species remain in the finished part. This has the effect of protracting the process duration, especially if the initiator composition is kept low so as to minimize rate of heat generation. In free radical polymerization, this problem is further exacerbated by the reaction inhibition which occurs as a result of the presence of oxygen (either dissolved in the polymerizing liquid, or present in the vapor space surrounding the mold). Nitrogen purging of both the polymerizing liquid and of the mold cavity must be employed to keep oxygen levels low so that polymerization may occur in a timely fashion. Often nitrogen purging is not able to remove all oxygen, and parts remain only partially cured, especially near the part surfaces, leading to sticky or tacky skins. Manufacturers have gone to great lengths in order to prevent oxygen from slowing the cure reaction in the near-surface region of cast parts, often employing initiators that react with oxygen diradicals, high levels of initiators (which increases the likelihood of high-temperature excursions and yellowing), or oxygen impermeable films at the surfaces of the cured parts. Insertion of such films entails opening the mold after partially curing the object, which further has the effect of complicating the process and protracting the process duration.

SUMMARY OF THE INVENTION

The present invention discloses a revolutionary approach that overcomes the above described intrinsic drawbacks of commercially established processes. It is unique in that it has the promise of becoming an extremely economical process suitable for mass manufacture. It also gives parts that are dimensionally exact. Another aspect of this disclosure is the formulation of a new class of polymerizable materials that exhibit a semi-solid-like behavior during molding, very low inherent shrinkage upon curing, and highly optimized engineering properties of the final object.

More particularly, this invention is directed to a process for the rapid in-situ near-net-shape polymerization of semi-solid-like materials to provide a cured resin material characterized by one or more macromolecular networks resulting in articles of manufacture that are dimensionally stable and precise, with very little shrinkage upon cure. The process includes the steps of mixing together a dead polymer, a reactive plasticizer and an initiator to give a semi-solid polymerizable composition; shaping the semi-solid composition into a desired geometry; and exposing the polymerizable composition to a source of polymerizing energy, to give a final product with dimensional stability and high-fidelity replication of an internal mold cavity. The article so produced can optionally be transparent and/or have resistance to impact (resilient). The resulting macromolecular network is characterized as having either i) a semi-interpenetrating crosslinked polymer network of reactive plasticizer wrapped around and within an entangled dead polymer (semi-IPN); or ii) an interpenetrating crosslinked polymer network of reactive plasticizer within an entangled dead polymer, the reactive plasticizer polymer network being further crosslinked to the dead polymer; or iii) inter-penetrating reactive plasticizer polymer chains, which may be linear, branched, etc., within an entangled dead polymer. In the extreme, very little to none of the dead polymer is used and only reactive oligomers or reactive macromers are used, as long as the material can be handled as a semi-solid. Upon polymerization, this arrangement leads to an entangled polymer (linear, branched, etc.) or to a single, uniform, crosslinked polymer network.

The reactive plasticizer may react with the dead polymer chains if the polymer has crosslinkable groups. In the presence of multifunctional monomers, two polymer networks are formed that are crosslinked together. Grafting reactions by chain transfer to the dead polymers may also occur in addition to the reactive plasticizer network formation among the dead polymers. Such systems are desirable because crosslinking of the dead polymer to the network formed by the reactive plasticizer can prevent phase separation between the two polymers. If only mono-functional reactive plasticizers are used, linear polymeric chains may be formed among the dead polymer chains. This arrangement will generally not be preferred over the crosslinked network for preparing transparent parts because uncrosslinked polymers tend to phase separate over time (kinetically limited), except in rare cases of compatibility between the two or more polymeric phases. Mixtures containing only mono-functional reactive plasticizers will often react slightly with the dead polymer chains (even when no crosslinkable side groups are present on the dead polymer), desirably producing a slightly crosslinked network having sufficient stability to prevent phase separation over time periods of interest. When a non-transparent finished part is the objective, then the above limitations are relieved.

The invention further encompasses certain semi-solid-like polymerizable compositions useful with the process. The semi-solid compositions comprise a mixture of a reactive plasticizer, an initiator and, optionally, a dead polymer. The compositions may optionally include other additives well-known in the art to effect mold release, improved stability or weatherability, non-yellowing properties, and the like.

This invention permits a broad selection of reaction chemistries to achieve precision parts with the required mechanical, thermal, optical and other desired properties. It obtains precision parts that are stress-free and flawless, with little or no birefringence. Precision products can be manufactured that are very impact-resistant or that have a prismatic geometry, or have other desirable but previously difficult-to-achieve characteristics.

DETAILED DESCRIPTION OF THE INVENTION

The terms "a" and "an" as used herein and in the appended claims mean "one or more".

The term "(meth)acrylate" as used herein and in the appended claims refers to both acrylate and methacrylate.

The term "dead polymer" as used herein and in the appended claims refers to a substantially fully polymerized, generally non-reactive polymer. The term "substantially fully polymerized" as used herein and in the appended claims refers to polymers that are at least 95% polymerized and preferably at least 98% polymerized. When certain polymer chemistries are used, the dead polymer may react with a reactive plasticizer, even if the dead polymer does not have unsaturated entities within or attached to the chain. The dead polymer may be linear or branched, homopolymer or copolymer. In the case of a copolymer, the sequence distribution may be random in sequence or blocky. The block copolymers may be tapered, or may have grafted side chains. The architecture of the dead polymer may be branched, multi-chain, comb-shaped or star-shaped, either symmetrical or non-symmetrical. Di-block, tri-block or multi-block structures all fall within the scope of this invention.

The semi-solid polymerizable composition useful in the production of precision parts is prepared, in one embodiment, by mixing the dead polymer with at least one small-molecule species, which is itself polymerizable or crosslinkable. This small-molecule species is referred to herein and in the appended claims as a "reactive plasticizer". In another embodiment, the semi-solid polymerizable core composition comprises a reactive plasticizer or a mixture of reactive plasticizers, without the presence of a dead polymer. The reactive plasticizer may encompass monomers, crosslinkers, oligomeric reactants, oligomeric crosslinkers, or macromeric reactants or macromeric crosslinkers (collectively macromers). The reactive plasticizer plasticizes the dead polymer to give a composition having the desired consistency at ambient temperature or below (i.e., able to maintain a shape for easy handling over short time periods), and at the processing temperature (i.e., malleable enough to be compressed or formed into a desired shape). The said processing temperature can be chosen conveniently to be moderately above or below ambient temperature. Alternatively, it may be preferable to formulate the reactive semi-solid compositions of the present invention using only reactive plasticizers that are low molecular weight polymers or oligomers that still possess reactive groups capable of later polymerization. In this case, the reactive plasticizer should be a longer chain molecule, of from about 1 to about 1000 repeat units, and preferably between about 1 and about 100 repeat units. These reactive plasticizers (or mixture of reactive plasticizers) have a high viscosity, preferably of greater than 1000 centipoise, at the temperature at which the material is to be handled (e.g., inserted into a mold cavity) to exhibit semi-solid behavior. Such a composition still falls within the scope of this invention because in this case a lower molecular weight distribution is used to achieve the desired viscosity reduction versus plasticization of a dead polymer with a reactive plasticizer. The reactive plasticizers can be mixtures themselves, composed of mono-functional, bi-functional, tri-functional or other homogeneous or heterogeneous multi-functional entities (heterogeneous reactive plasticizers being those that possess two or more different types of reactive functionalities).

In total, the amount and composition of the reactive plasticizer in the resulting formulation are such that the formulation is semi-solid-like and can be effectively handled with no need for a gasket in the mold. That is, the reactive plasticizer is present in concentrations sufficient to allow malleability and moldability at the desired processing temperature and pressure; however, the mixture is non-dripping and not free-flowing over short time periods at the material storage temperature and mold closure temperature, which can be conveniently chosen to be at ambient temperatures, or slightly above or below. The amount of reactive plasticizer is generally about 0.1% to about 100% by weight, preferably from about 1% to about 50%, more preferably from about 3% to about 25%.

The types and relative amounts of reactive plasticizer and dead polymer will dictate the time and temperature-dependent visco-elastic properties of the mixture. The visco-elastic properties of the chosen compositions may be wide and varied. For the practice of the invention as disclosed herewith, it is only required that the composition be highly viscous, semi-solid or solid-like for handling and/or insertion into a mold assembly at some temperature, while being semi-solid or liquid-like (i.e., deformable) at the processing temperature to which the mold assembly is heated or cooled after closure. Since virtually all known material systems become more compliant upon heating, the molding temperature will usually, but not necessarily, be equal to or higher than the handling temperature. In principle, any reactive plasticizer system (with or without dead polymer) which can be handled as a semi-solid or solid at some temperature, and which can be made to conform to a desired geometry (with or without changing the temperature and/or using force), can be used for the practice of the invention.

If the mixture consists mostly or wholly of reactive plasticizers, it may need to be cooled or partially cured in order to achieve the semi-solid-like consistency desirable for handling. Likewise, the mold-assembly temperature (the temperature at which the semi-solid composition is inserted into the mold) may desirably be below ambient temperature to prevent dripping or leaking from the mold prior to closure. Once the mold is closed, however, it may be compressed and heated to any pressure and temperature desired to induce conformation of the material to the internal mold cavity, even if such temperatures and pressures effect a free-flowing composition within the mold cavity (i.e., a composition which becomes free-flowing at the molding temperature is not precluded, and may be desirably chosen for the molding of fine-featured parts in which the molding compound must fill in small cavities, channels, and the like).

Alternatively, the dead polymer and reactive plasticizer mixture may be chosen and mixed in such proportions so as to form a composition that is glassy and rigid at ambient temperatures. Such a material will have all the benefits of ease of handling as a semi-solid composition, and will only require that the mold temperature after closure be adjusted to the softening temperature of the mixture in order to allow sufficient deformation of the material so that it may assume the desired shape (optionally in conjunction with applied pressure).

The composition most desirable for the practice of the invention will typically consist of about 3% to about 25% of a reactive plasticizer in a dead polymer. Once combined, said preferable mixture should provide a composition that is semi-solid at room temperature, such that it may be easily handled as a discrete part or object without undue stickiness or deformability. The mixture may be more easily homogenized at an elevated temperature and discharged into discrete parts which roughly approximate the desired shape of the final object, then cooled for handling or storage. When said preferable mixture or parts are placed into a mold and heated slightly above ambient temperature, or otherwise shaped or compressed while simultaneously heated, they will deform into the desired geometry without undue resistance. Such a composition is preferable in that handling and storage may occur at room temperature, while molding or shaping into the desired geometry may occur at temperatures only slightly or moderately removed from ambient. This and other benefits of the invention will be disclosed in more detail herewith.

When used without a dead polymer or with only a small amount of dead polymer, the reactive plasticizer should be a reactive oligomer or a reactive short polymer, having at least one reactive functional group. In this case, the reactive plasticizer should be a longer chain molecule, of from about 1 to about 1000 repeat units, and preferably between about 1 and about 100 repeat units. These reactive plasticizers (or mixture of reactive plasticizers) have a high viscosity, preferably of greater than 1000 centipoise, at the temperature at which the material is to be handled (e.g., inserted into a mold cavity) to exhibit semi-solid behavior. In the case of low molecular weight reactive plasticizers, the mixture may first be slightly polymerized to create the semi-solid consistency required for downstream processing as disclosed in this invention. Alternatively, the mixture may be cooled to create the semi-solid consistency.

Polymerization initiators are added to the mixture to trigger polymerization after molding. Such initiators are well-known in the art. Optionally, other additives may be added, such as mold release agents to facilitate removal of the object from the mold after curing, non-reactive conventional plasticizers or flexibilizers, pigments, dyes, organic or inorganic fibrous or particulate reinforcing or extending fillers, thixotropic agents, indicators, inhibitors or stabilizers (weathering or non-yellowing agents), UV absorbers, surfactants, flow aids, chain transfer agents, and the like. The initiator and other optional additives may be dissolved in the reactive plasticizer component prior to combining with the dead polymer to facilitate complete dissolution into and uniform mixing with the dead polymer. Alternatively, the initiator and other optional additives may be added to the mixture just prior to polymerization, which may be preferred when thermal initiators are used.

The ingredients in the semi-solid polymerizing mixture can be blended by hand or by mechanical mixing. The ingredients can preferably be warmed slightly to soften the dead polymer component. Any suitable mixing device may be used to mechanically homogenize the mixture, such as blenders, kneaders, extruders, mills, in-line mixers, static mixers, and the like, optionally blended at temperatures above ambient temperature, or optionally blended at pressures above or below atmospheric pressure.

In one presently preferred embodiment of the invention, an optional waiting period may be allowed during which the ingredients are not mechanically agitated. The optional waiting period may take place between the time the ingredients are initially metered into a holding container and the time at which they are homogenized mechanically or manually. Alternatively, the ingredients may be metered into a mixing device, said mixing device operated for a sufficient period to dry-blend the ingredients, then an optional waiting period may ensue before further mixing takes place. The waiting period may extend for an hour to one or more days. The waiting period may be chosen empirically and without undue experimentation as the period that gives the most efficient overall mixing process in terms of energy consumption. This embodiment of the invention may be particularly beneficial when the polymerizable mixture contains a high fraction of the dead polymer ingredient, especially when the dead polymer is glassy or rigid at ambient temperatures. Utilization of a waiting period may also be particularly beneficial when the dead polymer is thermally sensitive and so cannot be processed over an extended time at temperatures above its softening point without undue degradation, or when one or more of the reactive plasticizers is particularly volatile and so cannot be easily mixed with a high-melting-temperature polymer without undue evaporative loss of the reactive plasticizer.

By "semi-solid" and "semi-solid-like" are meant that, in essence, the polymerizable composition is a rubbery, taffy-like mass at sub-ambient, ambient, or elevated temperatures. Preferably the semi-solid mass has a sufficiently high viscosity to prevent dripping at ambient temperatures and pressures or below, but is malleable and can easily deform and conform to mold surfaces if the mold cavity is slightly heated or as a result of pressure exerted by pressing the two mold halves together, or a combination of both heat and pressure. The advantage of this semi-solid composition is that it can be pre-formed into a slab, disk, ball, or sheet, for example, which may in turn pressed between mold halves to define a lens or other object without an intervening gasket. Alternatively, a glob of this composition can be applied at slightly elevated temperature on one side of a mold cavity. The other mold half is then brought into contact with the semi-solidified mass, which is squeezed into the final desired shape by the approaching mold halves. Again, there is no need for gasketing of the mold halves, as the composition will not run out of the mold due to its viscous semi-solid-like nature (except that which is squeezed out in clamping the mold shut). Furthermore, the shaped mass may be kept at a slightly elevated temperature after mold closure to anneal away the stresses (birefringence), if any, introduced by squeezing, before the system is exposed to a source of polymerizing energy (such as UV light or temperature) to trigger network formation (curing).

With or without the annealing step, the assembly (i.e., the front mold, the rubbery precursor polymerizable composition, and the back mold) can then be exposed to UV or heat or another polymerizing energy source to complete polymerization of the reactive plasticizers in the mixture. The reactive plasticizers set up a semi-interpenetrating polymer network within an entangled dead polymer network. In some cases, the reactive plasticizer may react with groups on the dead polymer chain to form completely crosslinked networks. Optimization of engineering properties can be accomplished by the judicious quantitation of the architecture of the reactive molecules, their concentration and composition.

In case the edges of the finished parts require dimensional precision, then a precisely matched (or measured) amount of the reaction glob (mass) must be used. The front and back mold halves can be fashioned in such a way as to allow precise telescopic fit of one within the other. In one embodiment of this invention, the semi-solid material may be placed in about the center of the mold so that when the molds are compressed together, the semi-solid will flow radially outward towards the mold edges. Such a configuration allows the semi-solid material to fill in the gap between the mold while reducing or eliminating the entrainment of bubbles, air pockets, or other void defects. During mold closure, excess material (if any) can overflow the tiny annular region and be easily trimmed off after cure. If the amount of mass discharged into the mold cavity is measured very precisely, such flash can be eliminated altogether for repetitive production of identical finished objects. Alternatively, the molds may be designed so that the compressed semi-solid material only fills in part of the mold cavity, leaving the outer edges unfilled for example. In any case, the separation distance between the molds may be easily monitored so as to control the thickness of the molded part. Part thicknesses may easily range from microns to tens of centimeters with virtually no change in processing conditions or material formulations.

If the reactive plasticizers can be designed to conservatively exhibit a total shrinkage in the neighborhood of 8% when cured in their pure state, then a mixture containing less than 50% of such plasticizers in dead polymers will give only a very small (less than 4%) total shrinkage, assuming linear property additivity. This amount of total shrinkage is manageable by most curing regimens, including blanket UV exposure (for photo-cure) and rapid temperature spikes (for thermal-cure). In certain realistic cases, the intrinsic shrinkage of oligomeric reactive plasticizers may be about 5%, yet the maximum amount used in the formulation for plasticization may be only 10% by weight, giving rise to a system than shrinks approximately 0.5%. In certain other realistic cases, the intrinsic shrinkage of small molecule reactive plasticizers may be about 10%, yet the maximum amount used in the formulation for plasticization may be only 5% by weight, again giving rise to a system than shrinks approximately 0.5%.

Even in the case where 50–100% reactive plasticizers are present, low shrinkage may be realized because the system is not now limited to non-viscous, flowable components. In the prior art, material systems were limited by low-viscosity requirements, which inherently translates to systems possessing a high population of reactive entities and therefore exhibiting large shrinkage upon cure. Because low viscosity is no longer a requirement with the practice of the present invention, semi-solid material systems with high viscosity, optionally high molecular weight, and inherently low shrinkage may now be utilized.

The molding compositions of the invention thus display low shrinkage upon cure. By "low shrinkage" is meant that the shrinkage of the composition of the invention upon cure will typically be less than about 5%, preferably less than about 2%. This benefit enables molding processes in which the fabricated part shows high replication fidelity of the mold cavity. That is, because shrinkage of the polymerizable formulation is quite small (typically less than 5%, more preferably less than 2%), the cured part will retain the shape of the mold cavity throughout cure. Problems associated with shrinkage such as premature mold release, which greatly hinder and complicate current state-of-the-art practices, are eliminated. Note that the present invention can also be practiced with other types of polymerizable systems, such as those initiated with ionic initiators, microwaves, x-rays, e-beams, or gamma radiation. In addition, condensation, ring-opening and other polymerization mechanisms may be similarly practiced.

The high replication fidelity achieved with the invention disclosed herewith may be appreciated in the casting of optical components which rely on precise, smooth surfaces such as ophthalmic lenses, contact lenses, prisms, optical disks and the like. High fidelity replication may be also appreciated in the molding of components that rely on surfaces having desired exact topographies, such as optical storage disks, printing plates or other pattern transfer media. High replication fidelity may be further appreciated in the molding of three dimensional or complex geometry components which require dimensionally precise replication from the mold such as couplers, housings, gears, various packaging assemblies, and the like.

It should be appreciated that the cross-linked interpenetrating polymer networks formed during the practice of the invention disclosed herewith provide continued dimensional precision during the use or operation of the molded part (i.e., dimensional stability). That is, the cross-linked networks do not flow when heated above their glass transition temperature, and provide improved resistance to chemical attack, repeated load cycles, and the like. The benefits of dimensional stability achieved with the practice of the invention will be appreciated by fabricators of all types of moldable objects which may benefit from precise geometries.

Another beneficial characteristic of the present invention is that free radical polymerization and other triggerable chain polymerization mechanisms (e.g., via the use of ionic initiators) proceed efficiently in semi-solid media because of reduced oxygen inhibition and slow termination reactions. Without being bound by theory, this is believed to be due in part to the decreased mobility of oxygen molecules in high-viscosity media. In addition, oxygen-scavenging additives may be incorporated into the polymerizable mixture prior to initiation of cure. Thus, semi-solid polymerizable mixtures allow processing in which the need for nitrogen purging during mixing and molding steps is reduced. Curing reactions will also proceed further to completion in the near-surface region of the object even when oxygen is present in the gas phase surrounding the object to be cured, thus reducing or eliminating the need for oxygen barrier layers at the surface of the molded part. UV initiators may further be chosen and incorporated in such concentrations so as to give rapid curing using UV-triggered polymerizations. By "rapid curing" is meant that the molded object may be substantially cured by UV light within about 1 hour, or as fast as a few minutes. Such curing regimens provide significantly faster curing cycles than the 8- to 24-hour curing cycle times typical in the current art.

Yet another beneficial characteristic of the disclosed invention is that thermal spikes produced by the polymerization of unsaturated species are mitigated. Conventional casting processes utilize low-viscosity systems, which contain near 100% reactive components. Such systems experience temperature spikes due to the exothermic curing reaction. When the entire part is irradiated and cured at once, part temperatures can increase rapidly by up to 200° C. over the part temperature prior to cure initiation due to the curing exotherm. Such temperature excursions lead to thermal degradation, discoloration, and part warpage upon being released from the mold due to thermal expansion-contraction effects.

The semi-solid-like nature of the polymerization mixture of this invention disclosed here greatly reduces such temperature spikes because the proportion of reactive components in the system is typically less than 50% by weight, and preferably less than 25% by weight, thereby substantially reducing the exotherm during cure. Thus, a mixture with only 25% by weight of the reactive plasticizer component will rise at most approximately 50° C. Such temperature rises are easily withstood by most material formulations, and further, such a small temperature excursion precludes part warpage after mold release. Even when the amount of reactive plasticizer is above 50%, the semi-solid compositions will typically possess a low population of reactive entities, thus mitigating high temperature excursions and associated problems. Reduced exotherms will be appreciated by fabricators of precise, moldable objects, especially when parts containing thermally-sensitive constituents, or those having thick cross sections are to be fabricated.

This process enjoys the benefits of (1) material formulation flexibility, (2) finished parts being thermosets with interpenetrating networks or slightly crosslinked networks, (3) room temperature or slightly elevated temperature processing, (4) UV curing (photo-polymerization) that is not limited by heat transfer time or long cycle time, (5) rapid, efficient, low-oxygen-inhibited polymerization carried out in semi-solid media, (6) minimal temperature rise due to exothermic reactions, (7) low pressure operation, and (8) either continuous process or batch-wise operation with an intermediate step of casting from pre-forms (e.g., disks, slabs, balls, or pucks).

Two example process schemes are discussed below. Numerous variants can be envisioned by those skilled in the art of polymerization reaction engineering and polymer processing and molding. Hence, the present invention is not limited by these two example processing embodiments.

Batchwise processing provides precision-casting from pre-forms. A dead polymer, a reactive plasticizer, and an initiator package (optionally including other additives such as anti-oxidants, stabilizers, and the like) are mixed together (optionally with a waiting period during which the ingredients are not mechanically agitated) in a mixer equipped with temperature control and vacuum capabilities, to form a semi-solid polymerizable composition free of voids or air bubbles. The semi-solid composition is discharged from the mixer, and the discharge is cast into slabs (disks, pucks, balls, buttons, sheets, and the like), which serve as pre-forms for the subsequent precision casting operation. Alternatively, an extruded strand of the semi-solid composition can be sliced or diced into pre-forms. In a downstream operation, the pre-forms (which may be stored at room temperature or refrigerated temperatures in the interim, or which may even be partially cured to facilitate handling and storage) can be retrieved and shaped into the desired geometry for production of the final article. In a presently preferred embodiment, the pre-forms are placed in about the center of and sandwiched between two mold halves, whereupon the mold is closed, briefly heated to enhance material compliance as necessary, and flood-exposed by UV- or heat-cured. One can envision this processing scheme to suit just-in-time production situations, where an inventory of pre-forms can be used to make precise parts upon demand. In situations where a large variety of parts must be made just-in-time, this approach offers great ease of material handling. Eye glass lenses or contact lenses having a large range of prescriptions constitute one such example where this batchwise process scheme is appropriate.

In an alternative, continuous process, the dead polymer, the reactive plasticizer, and the initiator package (optionally including other additives such as anti-oxidants, stabilizers, and the like) are mixed together in an extruder. There is optionally a waiting period prior to the material being introduced into the extruder, during which time the ingredients are in intimate contact with one another, but are not mechanically agitated. Periodically, the extruder discharges a fixed amount of semi-solid reactive plasticizer-dead polymer composition as a warm glob into approximately the center of a temperature-controlled mold cavity (or in such other manner that voids, bubbles, weld lines, and the like are minimized during the molding process). The mold, which exhibits a telescopic fit of the front/back mold assembly, is then closed. An optional waiting period may ensue at the still-elevated temperature to anneal any stresses induced by squeezing of the glob. Finally, the captured material is flood-exposed by UV or heat-cured. This second example process flow is best suited for situations where the number of different parts is small, but each part is mass manufactured into many copies. Precision optics constitute one potential application area, as well as many engineering parts with intricate geometries found in sporting goods, automotive, construction and aerospace, etc., industries.

Material Design Considerations

There exist in the literature at least four basic ways to develop a new polymer system with unique properties: (1) synthesize new monomers, (2) develop new methods and techniques of polymerization, (3) combine known monomers/crosslinkers in such a way that the resulting material has superior attributes, and (4) combine known polymers into blends or alloys. In the present invention, we concentrate on a fifth, new approach, i.e., the combination of dead polymers with monomeric or oligomeric reactive diluents. These reactive diluents, when used in small amounts, actually serve the role of plasticizers. Instead of inert plasticizers that simply remain in a plastic to soften the material, the reactive diluents/plasticizers can initially soften the polymer to facilitate the molding process (allowing for lower temperature molding processes compared with the processing of conventional, unplasticized thermoplastic materials); but, upon curing, the polymerized reactive plasticizers lock in the precise shape and morphology of the polymer within the cured resin (and also lock in the reactive plasticizers themselves so that they cannot leak or be leached out of the resin overtime).

Once polymerized, the reacted plasticizers typically no longer soften the dead polymer to the same extent as before curing. The hardness of the cured resin will be determined by the chemical structure and functionality of the reactive plasticizers and dead polymers used, their concentration, molecular weight, and the degree of crosslinking and grafting to the dead polymer chains. Additionally, chain terminating agents can be added to the formulation prior to polymerization in order to limit the molecular weight and degree of crosslinking of the polymer formed by reacting the plasticizers, thus adding a measure of control in altering the final mechanical properties of the cured parts. At the same time polymerization results in no significant shrinkage (due to the overall low concentration of the reactive plasticizer or the low population of reactive entities), so the finished objects remain dimensionally stable, yielding high fidelity replication of the mold cavity. Precise geometric replication of the mold cavity is further preserved due to the relatively low molding temperatures and reduced exotherm from polymerization, which is particularly applicable to part designs having thick cross-sections.

Subsequent discussions concerning the basic material design considerations are divided into two categories based on the type of dead polymer utilized in the process. One category begins with standard thermoplastics as the dead polymer. These include, but are not limited to, polystyrene, polymethylmethacrylate, poly(acrylonitrile-butadiene-styrene), polyvinyl chloride, polycarbonate, polysulfone, polyvinylpyrrolidone, polycaprolactone, and polyetherimide, for example. The thermoplastics may optionally have small amounts of reactive entities attached (copolymerized, grafted, or otherwise incorporated) to the polymer backbone to promote crosslinking upon cure. They may be amorphous or crystalline. They may be classified as high performance engineering thermoplastics (e.g., polyether imides, polysulfones, polyether ketones, etc.), or they may be biodegradable (starch, prolamine, and cellulose, for example). These examples are not meant to limit the scope of compositions possible during the practice of the current invention, but merely to illustrate the broad selection of thermoplastic chemistries permitted under the present disclosure. Reactive plasticizers may be mixed with a thermoplastic polymer such as those listed above to give a semi-solid-like composition that can be easily molded into dimensionally precise objects. Upon polymerizing to form a cured resin, the dimensional stability of the object is locked in to give exact three-dimensional shapes or precise surface features. Thermoplastic polymers may be chosen in order to give optical clarity, high index of refraction, low birefringence, exceptional impact resistance, good thermal stability, high oxygen permeability, UV transparency or blocking, low cost, or a combination of these properties in the finished, molded object.

The other category utilizes "thermoplastic elastomers" as the dead polymer. An exemplary thermoplastic elastomer is a tri-block copolymer of the general structure "A-B-A", where A is a thermoplastic rigid polymer (i.e., having a glass transition temperature above ambient) and B is an elastomeric (rubbery) polymer (glass transition temperature below ambient). In the pure state, ABA forms a microphase-separated morphology. This morphology consists of rigid glassy polymer regions (A) connected and surrounded by rubbery chains (B), or occlusions of the rubbery phase (B) surrounded by a glassy (A) continuous phase, depending on the relative amounts of (A) and (B) in the polymer. Under certain compositional and processing conditions, the morphology is such that the relevant domain size is smaller than the wavelength of visible light. Hence, parts made of such ABA copolymers can be transparent or at worst translucent. Thermoplastic elastomers, without vulcanization, have rubber-like properties similar to those of conventional rubber vulcanizates, but flow as thermoplastics at temperatures above the glass transition point of the glassy polymer region. Melt behavior with respect to shear and elongation is similar to that of conventional thermoplastics. Commercially important thermoplastic elastomers are exemplified by SBS, SIS, and SEBS, where S is polystyrene and B is polybutadiene, I is polyisoprene, and EB is ethylenebutylene copolymer. Many other di-block or tri-block candidates are known, such as poly(aromatic amide)-siloxane, polyimide-siloxane, and polyurethanes. SBS and hydrogenated SBS (i.e., SEBS) are well-known products from Shell Chemicals (Kraton®). DuPont's Lycra® is also a block copolymer.

When thermoplastic elastomers are chosen as the starting dead polymer for formulation, exceptionally impact-resistant parts may be manufactured by mixing with reactive plasticizers. The thermoplastic elastomers, by themselves, are not chemically crosslinked and require relatively high-temperature processing steps for molding which, upon cooling, leads to dimensionally unstable, shrunken or warped parts. The reactive plasticizers, if cured by themselves, may be chosen to form a relatively glassy, rigid network, or may be chosen to form a relatively soft, rubbery network, but with relatively high shrinkage. When thermoplastic elastomers and reactive plasticizers are blended together and reacted to form a cured resin, they form flexible networks with superior shock-absorbing and impact-resistant properties. By "impact-resistant" is meant resistance to fracture or shattering upon being struck by an incident object. Depending on the nature of the dead polymer and reactive plasticizers used in the formulation, the final cured resin may be more stiff or more stretchy than the starting dead polymer. Composite articles exhibiting exceptional toughness may be fabricated by using a thermoplastic elastomer which itself contains polymerizable groups along the polymer chain, such as SBS tri-block copolymers, for example.

Furthermore, when compatible systems are identified, transparent objects can be cast. "Compatibility" refers to the thermodynamic state where the dead polymer is solvated by the reactive plasticizers. Hence, molecular segments with structural similarity would promote mutual dissolution. Aromatic moieties on the polymer generally dissolve in aromatic plasticizers, and vice versa. Hydrophilicity and hydrophobicity are additional considerations in choosing the reactive plasticizers to mix with a given dead polymer. Even when only partial compatibility is observed at room temperature, the mixture often becomes uniform at a slightly increased temperature; i.e., many systems become clear at slightly elevated temperatures. Such temperatures may be slightly above ambient temperatures or may extend up to the vicinity of 100° C. In such cases, the reactive components can be quickly cured at the elevated temperature to "lock-in" the compatible morphology in the cured resin before system cool-down. Hence, both material and processing approaches can be exploited to produce optically clear parts. Optically clear and dimensionally exact parts have a wide range of potential applications. For example, optically clear materials such as polycarbonate, polystyrene, polymethyl methacrylate, polysulfone, polyphenylene oxide, polyethylene terephthalate, polyolefins, thermoplastic elastomers, polyurethanes, and variations, copolymers, and/or mixtures thereof can be employed to create useful formulations by mixing with suitable reactive plasticizer packages. Optically transparent phase-separated systems may be beneficial prepared by combining a phase-separated iso-refractive mixture as the dead polymers in the system. When a reactive plasticizer is added which either (1) partitions itself approximately equally between the phases or (2) has a refractive index upon polymerizing similar to that of the dead polymer mixture, a clear part results upon curing. Alternatively, when the reactive plasticizer does not partition itself equally between the phases and does not possess a refractive index upon curing similar to the polymer mixture, the refractive index of one of the phases may be altered to give a resultant iso-refractive mixture. With the process innovation described herewith, powerful new material systems can be developed.

A preferred formulation for developing optically clear and high impact-resistant materials uses cyclo-olefin polymers and/or cyclo-olefin copolymers (polyolefins) such as the cyclo-olefin Zeonor from Zeon Chemicals as a dead polymer. Formulations based on one or more of the Zeonor grades (1020R, 1060R, 1420R, 1600, etc.) exhibit excellent optical properties, impact resistance, thermal stability, good hardness, low water absorption, and low density (approximately 1.01 g/cc for the pure polymer).

Another preferred formulation for developing optically clear and high impact-resistant materials uses styrene-rich SBS tri-block copolymers that contain up to about 75% styrene. These SBS copolymers are commercially available from Shell Chemicals (Kraton®), Phillips Chemical Company (K-Resin®), BASF (Styrolux®), Fina Chemicals (Finaclear®), and Asahi Chemical (Asaflex®). In addition to high impact resistance and good optical clarity, such styrene-rich copolymers yield materials systems which preferably exhibit other desirable properties such as a relatively high refractive index (that is, the index of refraction is equal to or greater than about 1.54) and low density (their densities are less than about 1.2 g/cc, and more typically are about 1.0 g/cc).

When the mixture refractive index is an especially important consideration, high refractive index polymers may be used as one or more of the dead-polymer components. Examples of such polymers include polycarbonates and halogenated polycarbonates, polystyrenes and halogenated polystyrenes, polystyrene-polybutadiene block copolymers and their hydrogenated and halogenated versions (all of which may be linear, branched, star-shaped, or non-symmetrically branched or star-shaped), polystyrene-polyisoprene block copolymers and their hydrodrogenated and halogenated versions (including the linear, branched, star-shaped, and non-symmetrical branched and star-shaped variations), poly(pentabromophenyl (meth)acrylate), polyvinyl carbazole, polyvinyl naphthalene, poly vinyl biphenyl, polynaphthyl (meth)acrylate, polyvinyl thiophene, polysulfones, polyphenylene sulfides, urea-, phenol-, or naphthyl-formaldehyde resins, polyvinyl phenol, chlorinated or brominated polystyrenes, poly(phenyl $\alpha$- or $\beta$-bromoacrylate), polyvinylidene chloride or bromide, and the like. In general, increasing the aromatic content and the halogen content (especially bromine) are effective means well-known in the art for increasing the refractive index of a material. These properties are especially preferred for ophthalmic lenses as it enables the production of ultra thin, light-weight eyeglass lenses which are desirable for low-profile appearances and comfort of the wearer.

Alternatively, elastomers, thermosets (e.g., epoxies, melamines, acrylated epoxies, acrylated urethanes, etc., in their uncured state), and other non-thermoplastic polymeric compositions may be desirably utilized during the practice of this invention.

Mixtures of such materials may also be beneficially used to create dimensionally stable parts with desirable properties. For example, impact modifiers may be blended into various thermoplastics or thermoplastic elastomers to improve the impact strength of the final cured resin. In such cases, the presence of the reactive plasticizers will facilitate blending by lowering the softening temperature of the polymers to be blended. This is especially beneficial when a temperature-sensitive material is being blended with a high-$T_g$ polymer. When optically clear materials are desired, the mixture components may be chosen to have the same refractive index (iso-refractive) such that light scattering is reduced. When iso-refractive components are not available, the reactive plasticizers may also help reduce the domain size between two immiscible polymers to below the wavelength of light, thus producing an optically clear polymer mixture which would have otherwise been opaque.

The reactive diluents (plasticizers) can be used singly or, alternatively, mixtures can be used to facilitate dissolution of a given dead polymer. The reactive functional group can be acrylate, methacrylate, acrylic anhydride, acrylamide, vinyl, vinyl ether, vinyl ester, vinyl halide, vinyl silane, vinyl siloxane, (meth)acrylated silicones, vinyl heterocycles, diene, allyl and the like. Other less known but polymerizable functional groups can be investigated, such as epoxies (with hardeners) and urethanes (reaction between isocyanates and alcohols). In principle, any monomers may be used as reactive plasticizers in accordance with the present invention, although preference is given to those which exist as liquids at ambient temperatures or slightly above, and which polymerize readily with the application of a source of polymerizing energy such as light or heat in the presence of a suitable initiator.

Reactive monomers, oligomers, and crosslinkers that contain acrylate or methacrylate functional groups are well known and commercially available from Sartomer, Radcure and Henkel. Similarly, vinyl ethers are commercially available from Allied Signal. Radcure also supplies UV curable cycloaliphatic epoxy resins. Photo-initiators such as the Irgacure and Darocur series are well-known and commercially available from Ciba Geigy, as is the Esacure series from Sartomer. Thermal initiators such as azobisisobutyronitrile (AIBN), benzoyl peroxide, dicumyl peroxide, t-butyl hydroperoxide, and potassium persulfate are also well known and are available from chemical suppliers such as Aldrich. Vinyl, diene, and allyl compounds are available from a large number of chemical suppliers, as is benzophenone. For a reference on initiators, see, for example, Polymer Handbook, J. Brandrup, E. H. Immergut, eds., $3^{rd}$ Ed., Wiley, N.Y., 1989. Below we will use acrylates (and in a few cases, methacrylates) to illustrate the flexibility of our formulation approach. Similar structures with other reactive groups based on either small or large molecule architectures (such as acrylamides, vinyl ethers, vinyls, dienes, and the like) can be used in conjunction with the disclosed casting process.

The compatibility of dead polymer-reactive plasticizer mixtures is demonstrated by checking the optical transparency of the resulting material at room temperature or slightly above, as illustrated by Example 1 below. To demonstrate the great diversity of reactive plasticizers that can be used to achieve such compatibility, we will name only a few from a list of hundreds to thousands of commercially available compounds. For example, mono-functional entities include, but are not limited to: isodecyl acrylate, hexadecyl acrylate, stearyl acrylate, isobornyl acrylate, vinyl benzoate, tetrahydrofurfuryl acrylate (or methacrylate), caprolactone acrylate, cyclohexyl acrylate, methyl methacrylate, ethyl acrylate, propyl acrylate, and butyl acrylate, etc. Bi-functional entities include, but are not limited to: polyethyleneglycol diacrylate, polypropyleneglycol diacrylate, hexanediol diacrylate, Photomer 4200 (from Henkel), polybutadiene diacrylate (or dimethacrylate), Ebecryl 8402 (from Radcure), bisphenol A diacrylate, ethoxylated (or propoxylated) bisphenol A diacrylate. Tri-functional and multi-functional entities include, but are not limited to: trimethylolpropane triacrylate (and its ethoxylated or propoxylated derivatives), pentaerythritol tetraacrylate (and its ethoxylated or propoxylated derivatives), Photomer 6173 (a proprietary acrylated oligomer of multi functionality, from Henkel), and a whole host of aliphatic and aromatic acrylated oligomers from Sartomer (the SR series), Radcure (the Ebecryl series), and Henkel (the Photomer series).

When high refractive index materials are desired, the reactive plasticizers may be chosen accordingly to have high refractive indices. Examples of such reactive plasticizers, in addition to those mentioned above, include brominated or chlorinated phenyl (meth)acrylates (e.g., pentabromo methacrylate, tribromo acrylate, etc.), brominated or chlorinated naphthyl or biphenyl (meth)acrylates, brominated or chlorinated styrenes, tribromoneopentyl (meth)acrylate, vinyl naphthylene, vinyl biphenyl, vinyl phenol, vinyl carbazole, vinyl bromide or chloride, vinylidene bromide or chloride, bromoethyl (meth)acrylate, bromophenyl isocyanate, and the like.

EXAMPLES

The following examples are provided to illustrate the practice of the present invention, and are intended neither to define nor to limit the scope of the invention in any manner.

The Examples 1 to 8 below are designed to discover pairs of materials that exhibit thermodynamic compatibility prior to polymerization. Examples 9 to 11 show systems that remain optically clear upon photocuring, and further illustrate material systems exhibiting high refractive indices. Tertiary, quaternary, and multi-component mixtures can be formulated based on knowledge gleaned from binary experiments. Generally, diluents that are small molecules have a higher degree of shrinkage. But, they are also typically better plasticizers. On the contrary, oligomeric plasticizers shrink less, but they also show less solvation power and less viscosity reduction. Hence, mixtures of reactive plasticizers can be prepared to give optimized compatibility, processing, and shrinkage properties.

Example 1
Experimental Protocol

Dead polymers are added to a vial, pre-filled with a small quantity of the intended reactive plasticizer. Gentle heating is applied while stirring homogenizes the mixture. The resulting semi-solid-like mass is observed visually and optical transparency at various temperatures is recorded. Complete clarity is indicative of component miscibility. A faint haze suggests partial miscibility, and opacity equates to incompatibility (light scattering as a result of phase separation). Many pairs of dead polymer-reactive plasticizers can thus be investigated.

Examples 2 to 8 report several findings of system compatibility and partial compatibility, following this procedure.

Example 2
Kraton-Based Systems

The following polymers are studied using the protocol described in Example 1. The accompanying table summarizes the polymer characteristics.

TABLE 1

| Kraton type | Composition (%) | Description |
|---|---|---|
| G 1652 | SEBS (S:29/EB:71) | linear, low molecular weight |
| G 1650 | SEBS (S:29/EB:71) | linear, medium Mw |
| G 1657 | SEBS (S:13/EB:87) | linear |
| D 1102 | SBS (S:28/B:72) | linear, low Mw |
| D 4141 | SBS (S:31/B:69) | linear |
| D 4240p | (SB)$_n$ (S:44/B:56) | branched |
| D 1116 | (SB)$_n$ (S:21/B:79) | branched |
| D 1107 | SIS (S:14/I:86) | linear |

S = styrene, EB = ethylene butylene, B = butadiene, I = isoprene

Hexanediol diacrylate solvates all Kraton samples well except for G 1650, which shows partial miscibility. Photomer 4200 solvates D1102, D1107, D4141, D4240p, and G1657 at elevated temperatures. Photomer 4200 (an oligomeric diacrylate) solvates G 1652 partially. Polybutadiene dimethacrylate (Sartomer CN301) solvates D1116, D1102, and D4141 partially at elevated temperatures. Ebecryl 8402 solvates G 1657. Isodecyl acrylate is compatible with all of the above Kratons. Hexadecyl acrylate, lauryl acrylate, and stearyl acrylate solvate Kraton at elevated temperatures.

Other monomers that solvate Kraton include butyl acrylate, isooctyl acrylate, isobornyl acrylate, benzyl acrylate, tetrahydrofurfuryl acrylate, and vinyl benzoate. In general, aliphatic acrylates solvate rubbery Kraton well. Ethoxylated bisphenol A diacrylate (average molecular weight of 424) solvates Kraton D4240p, D1107, D4141, and D1102 only slightly.

Example 3
Styrene-Rich-SBS Systems

Kraton D1401P is a linear styrene-rich SBS tri-block copolymer. Reactive plasticizers that solvate Kraton D1401P include: vinyl benzoate; tetrahydrofurfuryl acrylate; benzyl acrylate; isobornyl acrylate; butyl acrylate; octyl acrylate; isodecyl acrylate; butanediol diacrylate; hexanediol diacrylate; and ethoxylated bisphenol A diacrylate.

To obtain thermodynamically compatible systems containing styrene-rich SBS tri-block copolymers, Kraton D1401P can be replaced by other SBS copolymers such as those that are commercially available from Phillips Chemical Company (K-Resin), BASF (Styrolux), Fina Chemicals (Finaclear), and Asahi Chemical (Asaflex).

Example 4
PMMA-Based Systems

This study is conducted with a polymethyl methacrylate (PMMA) sample of molecular weight 25,000. Many reactive plasticizers have been found compatible with PMMA. These are: Photomer 4200; Photomer 6173; many alkoxylated multifunctional acrylate esters, such as propoxylated glycerol triacrylate; urethane acrylates, such as Ebecryl 8402 (aliphatic) and Ebecryl 4827, 4849 and 6700 (aromatic); tetrahydrofurfuryl acrylate; benzyl acrylate; butyl acrylate; butanediol diacrylate; hexanediol diacrylate; octyldecyl acrylate; isobornyl acrylate; and ethoxylated bisphenol A diacrylate.

Example 5
Polystyrene-Based Systems

Acrylated plasticizers that solvate polystyrene include Photomer 4200, tetrahydrofurfuryl acrylate, isodecyl acrylate. Bisphenol A diacrylate, hexadecyl acrylate, and stearyl acrylate exhibit compatibility at elevated temperatures (approximately 100° C. for example).

Example 6
Polycarbonate-Based Systems

Bisphenol A diacrylate, alkoxylated bisphenol A diacrylate, cycloaliphatic epoxy resin, N-vinyl-2-pyrrolidinone, and tetrahydrofurfuryl acrylate, among others, have been found useful for the solvation of polycarbonate at elevated temperature. Several aromatic urethane acrylates can be mixed with the above compounds to aid the compatibility of the ingredients.

Example 7
ARTON-Based Systems

Reactive plasticizers that solvate ARTON FX4727T1 (JSR Corporation) are: benzyl acrylate; isobornyl acrylate; isobornyl methacrylate; butyl acrylate; octyl acrylate; isooctyl acrylate; isodecyl acrylate; lauryl acrylate; behenyl acrylate. Aliphatic acrylates solvate ARTON very well.

Example 8
ZEONEX-Based Systems

Octyldecyl acrylate, butyl acrylate, and isooctyl acrylate solvate Zeonex 480R (Nippon Zeon Co., Ltd). Isobornyl acrylate solvates Zeonex 480R and E48R, and Zeonor 1420R, 1020R and 1600R. Lauryl acrylate and behenyl acrylate solvate ZEONEX 480R and E48R at elevated temperature.

Example 9
Transparent Photo-Cured Systems

Mixtures containing the dead polymer, reactive plasticizer, and photoinitiator were mixed by the protocol described in Example 1. The amount of reactive plasticizer was typically 3% to 25% and the photoinitiator was 1% to 5% by weight. Example photoinitiators include Esacure KT046 from Sartomer and Irgacure 184 from Ciba Geigy.

The resulting semi-solid composition was slightly heated (less than or equal to about 100° C.), pressed between flat glass plates, and flood-exposed by UV light. Rapid polymerization was observed that led to a clear and solid-like material.

The examples of transparent photo-cured systems included: Kraton D1401P-based systems reported by Example 3; PMMA-based systems reported by Example 4; ARTON-based systems reported by Example 7. Kraton D1401P-based systems also showed exceptional impact-resistance.

Example 10
Transparent Photo-Cured Systems Having a High Refractive Index

A mixture containing a dead polymer, reactive plasticizer, and photoinitiator was mixed by the protocol described in Example 1, and was processed further as described in Example 9. The dead polymer was Kraton D1401P and the reactive plasticizer was benzyl acrylate, mixed at a ratio by weight of 88/12. Irgacure 184 was added to the mixture at 2 wt % based on the overall weight of the system. Upon UV cure, a flat sample having a thickness of 2.4 millimeters was produced, which showed 88% light transmittance at a wavelength of 700 nm. The refractive index of the cured sample was 1.578 at the sodium D line at room temperature.

Example 11
Transparent Systems Utilizing a Waiting Period

Kraton D1401P and isooctyl acrylate were added to a glass vial in the weight ratio 93/7. The capped vial was allowed to sit overnight. After 24 hours, the mixture was a clear, semi-solid mass. Irgacure 184 was added to the mixture at 2 wt % (based on the overall weight of the system), and was dissolved into the system while slightly heating and mixing manually. The resulting semi-solid mass was processed further as described in Example 9. Upon UV cure, a flat sample having a thickness of 2.3 millimeters was produced, which showed 90% light transmittance at a wavelength of 700 nm. The refractive index of the cured sample was 1.574 at the sodium D line at room temperature.

What is claimed is:

1. A method of forming an optical lens, the method comprising the steps of:
   a) mixing together an optically clear dead polymer, a reactive plasticizer in an amount to render the composition semi-solid and malleable, and an initiator to form a semi-solid polymerizable composition, wherein the dead polymer and the reactive plasticizer exhibit compatibility at temperatures not higher than 100° C., and wherein the polymerizable composition remains optically clear and exhibits low shrinkage when polymerized;
   b) shaping the semi-solid composition into a desired geometry; and
   c) exposing the semi-solid composition to a source of polymerizing energy;
to give the resultant optically clear lens comprising a crosslinked polymer network of reactive plasticizer within an entangled dead polymer.

2. A method according to claim 1 wherein the optically clear lens comprises a semi-interpenetrating crosslinked polymer network of reactive plasticizer within an entangled dead polymer.

3. A method according to claim 2 wherein the polymer network of reactive plasticizer is further crosslinked to the dead polymer.

4. A method according to claim 1 wherein the optically clear lens comprises interpenetrating reactive plasticizer polymeric chains within an entangled dead polymer.

5. A method according to claim 1 wherein the optically clear lens is impact-resistant.

6. A method according to claim 1 wherein the optically clear lens exhibits high fidelity replication.

7. A method according to claim 1 wherein the optically clear lens exhibits dimensional stability.

8. A method according to claim 1 wherein the optically clear lens is an ophthalmic lens.

9. A method according to claim 1 wherein the semi-solid composition is shaped by placing the semi-solid composition in contact with a mold, the mold corresponding to the desired geometry.

10. A method according to claim 9 wherein the semi-solid is shaped by placing it into about the center of the mold, such that shaping the semi-solid while optionally heating causes the semi-solid composition to flow radially outward.

11. A method according to claim 1 which further comprises the step of providing a waiting period at a predetermined temperature after the composition is shaped and before exposing to the source of polymerizing energy.

* * * * *